United States Patent [19]

Lindall

[11] 4,341,755

[45] Jul. 27, 1982

[54] PARATHYROID RADIOIMMUNOASSAY

[75] Inventor: Arnold W. Lindall, Marine on St. Croix, Minn.

[73] Assignee: Immuno Nuclear Corporation, Stillwater, Minn.

[21] Appl. No.: 169,492

[22] Filed: Jul. 15, 1980

[51] Int. Cl.$^3$ ............................... 424 12; G01N 33/56
[52] U.S. Cl. ..................................... 424/1; 23/230 B
[58] Field of Search ...................... 424/1, 12; 23/230 B

[56] References Cited

U.S. PATENT DOCUMENTS 4,146,602  3/1979  Gutcho et al. ........................... 424/1

OTHER PUBLICATIONS

Stewart et al., *Solid Phase Peptide Synthesis*, 2nd ed., Freeman & Co., 1968, pp. 1–26.
Lindall, Presentation Congesso Sanitario Delgi Ospedali Galliera, Oct. 1978.
Jaffe et al., *Methods of Hormone Radioimmunoassay*, 2nd ed., Academic Press, 1979, chapter 19.
Parthemore et al., J. Clin. Endo. Met., 47:248–289, (1978).
Di Bella et al., Clin. Chem., 24:451 ∝ 454, (1978).
Evr. J. Clin. Invest., 8:149–154, (1978).
Health, III et al., Clin. Chem., 24:1833–1835, (1978).
Di Bella et al., J. Clin. Endocrin. Met., 46:604–612.
Arnauld et al., J. Clin. Inves., 50:21–34, (1971).

*Primary Examiner*—Christine M. Nucker
*Attorney, Agent, or Firm*—Dorsey & Whitney

[57] ABSTRACT

A method for the radioimmunoassay of parathyroid hormone in mammalian serum. The method is an improvement on previous double antibody radioimmunoassays in that spurious assay results caused by the nonspecific interaction of serum proteins with the labeled peptide is eliminated by the labeling of a specific portion of either human or bovine parathyroid molecule. The 65-84 portion of human or bovine parathyroid hormone, as radioactively labeled, is incorporated in the assay as the labeled peptide. A chicken antibody with a high affinity for the 65-84 portion of human parathyroid hormone is incorporated in the assay as the first antibody. The invention further pertains to compounds useful in practicing the method, namely $X^{64}$-hPTH$^{65-84}$ and Y-$X^{64}$-hPTH$^{65-84}$ wherein X is either histidyl, tyramyl, histamyl, or tyrosyl, and wherein Y is either $^{125}$I or $^{131}$I.

119 Claims, 4 Drawing Figures

PARATHYROID RADIOIMMUNOASSAY

BACKGROUND OF THE INVENTION

1. Field of the Invention

This invention relates to radioimmunoassay measurement of the concentration of mammalian parathyroid hormone and certain fragments thereof in biological or other fluids.

2. Description of the Prior Art

Human parathyroid hormone (i.e. intact hPTH) is an 84 immuno acid sequence with a major role in maintaining the constancy (homeostasis) of calcium in cells and extracellular fluid, despite marked variations in calcium intake and excretion. Parathyroid peptides (both intact hPTH and certain hPTH fragments) are secreted from the parathyroid glands in response to a lowering of serum calcium; and, in the absence of parathyroid peptide secreting tumors, high levels of serum calcium inhibit secretion by the glands. Measuring parathyroid peptides in human serum has proven clinically to be an extremely helpful and efficient tool in the differential diagnosis and management of hypercalcemia; most notably, radioimmunoassay (i.e. RIA) can help to diagnose tumors and hyperplasia of the parathyroid glands. RIA detection of high blood levels of PTH peptides can establish that excess PTH secretion is causing hypercalcemia. RIA's can also be useful in localizing hyperfunctioning parathyroid tissue by assaying samples obtained via venous catheterization. PTH RIA is also useful for the diagnosis and management of hypocalcemia. With rare exceptions, hypocalcemic persons with deficient PTH (hypoparathyroidism) usually have subnormal blood concentrations of PTH peptides. Measurement of the concentration of PTH peptides in blood serum is frequently used to assess the status of renal osteodystrophy in renal failure patients on chronic dialysis. Serum PTH levels are often markedly elevated in patients with renal failure due to chronic negative calcium balance, hypocalcemia, and consequent secondary hyperparathyroidism.

In clinical parathyroid literature, a set of nomenclature has become common. N-terminal hPTH is the 1-34 amino acid sequence of hPTH. Antisera having a substantially high affinity for this sequence are referred to as N-terminal antibodies. Such antibodies will generally also have a high affinity for any sequence of amino acids incorporating the 1-34 amino acid sequence. Thus, such antibodies will have a high affinity for intact hPTH (i.e. hPTH$^{1-84}$) as well as N-terminal hPTH. C-terminal hPTH is the 35-84 amino acid sequence. Antisera having a substantially high affinity for the 35-84 sequence are referred to as C-terminal antisera. It is now well established that only small amounts of intact hPTH and even less free N-terminal hPTH are present in peripheral human serum. The main circulating hPTH peptide is C-terminal hPTH. Accordingly, RIA's are generally directed at C-terminal hPTH where the purpose is diagnosing hyperthyroidism and the other maladies recited above.

Prior art RIA's which measure the concentration of C-terminal hPTH in human serum are common; however, very few are available commercially. The commercially available assays generally involve the double antibody method. In brief, C-terminal hPTH (and lesser quantities of intact hPTH) present in human serum compete with a radioactively labeled peptide (generally radioactively labeled beef PTH$^{1-84}$) for a particular first antibody, thereby inhibiting the binding of the first antibody to the radioactively labeled peptide. As a result of the competitive inhibition, the ratio of first antibody bound labeled peptide to free labeled peptide diminishes as the concentration of C-terminal hPTH (and intact hPTH) increases. As a convenient method to circumvent the difficult task of separating bound labeled peptide from free labeled peptide, a second antibody is added that has a substantially high affinity for the first antibody and which forms a precipitate when bound to the first antibody bound labeled peptide. The quantity of second antibody added is generally only sufficient to bind a portion of first antibody found radioactively labeled peptide. The ratio of precipitated radioactively labeled peptide to non-precipitated radioactively labeled peptide similarly diminishes as the concentration of C-terminal hPTH (and intact hPTH) increases. The concentration of C-terminal hPTH (and intact hPTH) in an unknown sample is obtained by comparing the inhibition observed with the inhibition produced by known amounts of C-terminal hPTH (or intact hPTH), as presented in a standard curve. The concentration of C-terminal hPTH is generally represented as hPTH$^{1-84}$ equivalents. That is, the concentration in nanograms/ml (ng/ml) of serum is reported as if C-terminal hPTH were intact hPTH.

Most prior art double antibody PTH RIA's face a common difficulty in measuring the concentration of C-terminal hPTH: they often give a spurious value because of nonspecific interaction (NSI) of the labeled PTH peptide with serum proteins. That is, the labeled peptide is thought to react with various proteins present in the serum sample with the result that the first antibody, which ordinarily has a high affinity for the labeled PTH peptide, has a low or no affinity for the product of the reaction of the labeled PTH peptide with serum proteins.

In some prior art double antibody PTH RIA's, the standardized reagents used to prepare the standard curve do not contain human serum (Isotex Diagnostics, Friendswood, Texas 77546). In this case, standards are generally prepared by dissolving appropriate quantities of PTH peptides, whether human, beef, or of other sources, in an appropriate non-serum buffer. The NSI for the unknown sample of serum will depress the value of the ratio of precipitated to non-precipitated labeled PTH peptide, while there will be no similar depression for the standard reagents. This is so because the latter do not contain human serum and therefore the serum proteins which cause NSI are absent. Thus, the assay will indicate a concentration that is higher than the actual concentration. The error injected into assay results by NSI can be sufficiently great, on the order of several ng's/ml of hPTH$^{1-84}$ equivalents, to cause a mischaracterization of an unknown sample. That is, an assay of serum taken from a person with normal parathyroid glands could indicate hyperparathyroid disease.

Some prior art double antibody PTH RIA's seek to eliminate the effect of NSI on assay results. One prior art method (Arnaud, C. D., et al., 50 J. Clin. Invest. 21 (1971)) incorporates serum from hypoparathyroid patients or pooled serum stripped of PTH peptides in the standard reagents used to prepare the standard curve. This attempt to adjust for the effects of NSI on assay results is not wholly satisfactory. The serum added to the standard reagents is not the unknown serum to be tested. The concentration of serum peptides which give rise to NSI may vary significantly from person to person. Thus, depending upon whether the NSI for the unknown sample is relatively greater or less than the NSI for the serum incorporated in the standard reagents, the assay will indicate respectively concentrations lower or higher than the actual concentration. The error injected into this type of prior art assay can also be sufficiently great to mischaracterize an unknown sample.

Another PTH assay approach seeks to eliminate the effects of NSI on assay results by performing the RIA on significantly diluted serum. Diluting the serum in this manner does reduce NSI. However, while reducing the effect of NSI on assay results, diluting the serum generally reduces the sensitivity of the RIA to the degree that the RIA cannot detect the concentrations of C-terminal hPTH necessary to distinguish normal from abnormal functioning parathyroids.

At least one prior double antibody PTH RIA has adjusted for the effects of NSI while retaining the necessary sensitivity of the assay (PTH II, Immuno Nuclear Corp., Stillwater, Minn. 55082). In this RIA, an unknown sample of serum is divided into two portions. Intact PTH and C-terminal hPTH are removed from one of the two portions, leaving the serum proteins behind. Removing the intact hPTH and C-terminal hPTH in this manner is accomplished by binding the first antibody to a gel or resin to create a specific solid phase absorbent for intact PTH and C-terminal hPTH. However, removing the intact hPTH and C-terminal hPTH in this manner requires a full cycle of incubation of the portion of the serum to be stripped. Following this cycle of incubation, both the untouched portion of serum and the stripped portion of serum are assayed according to standard RIA methods. The stripped serum serves as a zero reference value to be subtracted from the result obtained with the untouched serum to yield results adjusted for NSI. While this method of stripping a portion of the very serum to be assayed compensates for NSI, it is not wholly satisfactory because it involves an extra cycle of incubation which increases the total time necessary to reach a final assay result after drawing a sample from a patient.

Double antibody PTH RIA's directed at human serum are primarily useful for diagnostic purposes and secondarily useful for research purposes. Similar double antibody PTH RIA's directed at the sera of mammals such as rats, oxen, or cows are particularly useful for advanced research on the functioning of parathyroids, because rats, oxen, and cows can be controlled and manipulated in ways inappropriate for human subjects. It is commonly known that most regions of bovine PTH and hPTH are structurally similar, and that fragments of bovine PTH are present in bovine parathyroid glands and circulate in the blood. Furthermore, it is now known that some regions of rat PTH and hPTH are structurally similar, and that fragments of rat PTH are present in rat parathyroid glands and circulate in rat blood. Because of these structural similarities, some antibodies have a substantially high affinity for bovine PTH, rat PTH, and hPTH. Thus, double antibody PTH RIA's incorporating such antibodies will measure the concentration of bovine PTH and rat PTH as well as hPTH. The effect of NSI on assay results is common to such RIA's whether directed to bovine serum, rat serum, or human serum. It is thought that NSI will similarly effect assays of any mammalian serum. Thus, the various attempts in prior art double antibody PTH RIA's to adjust for the effects of NSI are not wholly satisfactory when such RIA's are directed to mammalian serum.

SUMMARY OF THE INVENTION

The invention is based on the discovery that NSI can be eliminated in double antibody PTH RIA's directed to mammalian serum, especially bovine, rat, or human serum, by radioactively labeling only a selected fragment of the hPTH sequence or the bovine PTH sequence. A radioactively labeled fragment within the range of about 65–84 of bovine PTH or hPTH is incorporated in the assay as the labeled peptide. Accordingly, the invention includes a method for double antibody radioimmunoassay measurement of the concentration of PTH in biological fluids which comprises incorporating as the radioactively labeled peptide a radioactively labeled fragment within the range of about 65–84 of bovine PTH or hPTH, and compounds useful in practicing the method. The compounds include those having the formula $X^{64}$-$hPTH^{65-84}$ wherein X is a member of the group consisting of histidyl, tyramyl, histamyl, and tyrosyl and those having the formula $Y$-$X^{64}$-$hPTH^{65-84}$ wherein Y is a member of the group consisting of $^{131}I$ and $^{125}I$ and wherein X is a member of the group consisting of histidyl, tyramyl, histamyl, and tyrosyl.

Double antibody PTH RIA's incorporating radioactively labeled fragments within the range of about 65–84 of bovine PTH or hPTH follow methods otherwise common to double antibody RIA's. A first antibody must be found that has a high affinity for the particular radioactively labeled fragment and the PTH peptides to be measured. The unknown sample, the first antibody, and the radioactively labeled fragment are added together, or the addition of the radioactively labeled fragment is delayed for enhanced sensitivity of the assay. A second antibody is added which binds a portion of first antibody bound radioactively labeled fragment, thereby forming a precipitate. Precipitation may be accelerated according to conventional means with polyethylene glycol (PEG) and pre-precipitation with normal serum.

Radioactively labeled $hPTH^{65-84}$ is an example of a radioactively labeled fragment within the range of about 65–84 of hPTH. The fragment $hPTH^{65-84}$ may be radioactively labeled in many different ways, including adding a group that is receptive to known radioisotopes. Accordingly, $hPTH^{65-84}$ can be synthesized by solid state peptide chemistry, with, for example, a histidyl, tyramyl, histamyl, or tyrosyl (Tyr) group added at the 64th position of the hPTH sequence. The latter groups are receptive to radioiodine and other isotopes, which may be attached to the receptor groups according to conventional means. Thus, $^{125}I$-$Tyr^{64}$-$hPTH^{65-84}$ is an example of a radioactively labeled $hPTH^{65-84}$ and consequently is an example of a radioactively labeled fragment within the range of about 65–84 of hPTH.

The elimination of NSI for an RIA of the present invention is illustrated by comparing its assay of mammalian serum with that of a prior art RIA (PTH II, Immuno Nuclear Corp., Stillwater, Minn. 55082). The RIA of the present invention utilizes $^{125}I$-$Tyr^{64}$-$hPTH^{65-84}$ as the radioactively labeled peptide and an antibody, raised in chickens against intact bovine PTH, having a high affinity ($1 \times 10^{10}$ l/mol.) for $hPTH^{65-84}$. This first antibody consequently also has a high affinity for $^{125}I$-$Tyr^{64}$-$hPTH^{65-84}$, intact hPTH, and C-terminal hPTH. The prior art RIA utilizes radioiodinated intact bovine PTH and an antibody, raised in chickens against intact bovine PTH, having a high affinity for hPTH$^{44-64}$. This first antibody consequently also has a high affinity for radioiodinated intact bovine PTH, intact hPTH, and C-terminal hPTH.

To compare the RIA of the present invention with the prior art RIA, uremic human serum (with elevated C-terminal hPTH) was separated by a superfine G-75 Sephadex chromatograph. The contents of each eluate tube were divided into two portions to be assayed respectively by the two RIA's. In the area of tubes 20-25 (i.e. the void area containing no C-terminal hPTH), the prior art RIA showed approximately 4 ng/ml hPTH$^{1-84}$ equivalents (a spurious result attributable to NSI), while the RIA of the present invention showed no hPTH$^{1-84}$ equivalents (hence, no NSI).

The RIA of the present invention, incorporating $^{125}$I-Tyr$^{64}$-hPTH$^{65-84}$, will assay rat serum and bovine serum as well as human serum. This is so because its first antibody has a substantially high affinity for intact rat PTH and certain rat PTH fragments, and because the first antibody also has a substantially high affinity for intact bovine PTH and certain bovine PTH fragments. Serum proteins in rat, bovine, and human serum are thought to interact nonspecifically on the same region of the hPTH molecule when that molecule is radioactively labeled. Therefore, the RIA of the present invention by incorporating radioactively labeled hPTH$^{65-84}$, whether directed at rat, bovine, or human serum, excludes that region of the hPTH molecule which interacts with serum proteins. Thus, it does not suffer the adverse effects of NSI when directed to such sera.

NSI is similarly eliminated by incorporating as the radioactively labeled peptide radioactively labeled fragments within the range of about 65–84 of bovine PTH or hPTH. Serum proteins are thought to interact nonspecifically on a region of labeled hPTH molecules and labeled bovine PTH molecules at least somewhat removed from the region of 65-84. This is evidenced by the above comparison of the RIA of the present invention with the prior art RIA. NSI in the prior art RIA occurred somewhere in the region of 44-64. The antibody therein had an affinity for hPTH$^{44-64}$ and NSI suppressed binding of this antibody to labeled intact beef PTH. Accordingly, radioactively labeled peptides based on fragments smaller than hPTH$^{65-84}$ or bovine PTH$^{65-84}$ in such RIA's would also eliminate NSI. Moreover, fragments somewhat larger than hPTH$^{65-84}$ or bovine PTH$^{65-84}$ could serve as the basis for the radioactively labeled peptide. For example, radioactively labeled hPTH$^{63-84}$ or radioactively labeled bovine PTH$^{63-84}$ would also eliminate NSI in such RIA's. Based on general immunological principles, the first antibody of the RIA of the present invention will have a high affinity for fragments larger than hPTH$^{65-84}$ or bovine PTH$^{65-84}$ and may well have a high affinity for smaller fragments. Other antibodies could be raised with the requisite affinities should this particular first antibody not have a high affinity for certain smaller fragments.

DESCRIPTION OF THE PREFERRED EMBODIMENT

The following is a description of a typical preparation and operation of a double antibody PTH RIA which incorporates radioactively labeled hPTH$^{65-84}$. This RIA will assay rat, bovine, or human serum. It will also assay biological or other fluids.

PREPARATION OF STANDARD REAGENTS 0.1 M borate buffer (4.0 Liters)
  24.75 gm boric acid
  8.10 gm NaOH
  9.0 ml concentrated HCl
  Dissolve and dilute to 4.0 liters with distilled water. pH 8.4.

0.25 M borate buffer (1.6 Liters)
  24.75 gm boric acid
  8.10 gm NaOH
  9.0 ml concentrated HCl
  Dissolve and dilute to 1.6 liters with distilled water. pH 8.4.

5% BSA-0.25 M borate buffer (4.0 Liters)
  61.88 gm boric acid
  20.25 gm NaOH
  22.5 ml concentrated HCl
  665 ml 30% by volume BSA in distilled water (Bovine Serum Albumin available commercially from Sigma Chemical Co., St. Louis, Mo. 63178)
  8.0 ml 1% by volume merthiolate (thimersal) in distilled water.
  Dissolve and dilute to 4.0 liters with distilled water. pH 8.4.

5% BSA-0.25 M borate buffer in 0.22 M EDTA (100 ml)
  16.5 ml 30% BSA
  8.18 gm disodium EDTA (disodium ethylenediamine tetracetic acid dihydrate)
  0.2 ml 1% merthiolate
  Dissolve and dilute to volume of 100 ml with 0.25 M borate buffer; adjust pH to 8.4 with 40% by volume NaOH in distilled water.

1% BSA-0.1 M borate buffer (4.0 Liters)
  24.75 gm boric acid
  8.10 gm NaOH
  9.0 ml concentrated HCl
  133 ml 30% BSA
  1.6 ml 1% merthiolate
  Dissolve and dilute to 4.0 liters with distilled water. pH 8.4.

0.2 M acetic acid-ammonium acetate (500 ml)
  18 ml 1.0 M ammonium acetate
  82 ml 1.0 M acetic acid
  400 ml distilled water
  pH 4.0.

0.5 M Phosphate buffers (950 ml)
  (a) 68.1 g/liter KH$_2$PO$_4$
  (b) 89.0 g/liter Na$_2$HPO$_4$.2H$_2$O (or 71.0 g/liter anhydrous Na$_2$HPO$_4$)
  Mix 140 ml of (a) and 810 ml of (b) to obtain phosphate buffer of pH 7.4. Store at 2°-8° C. At those temperatures, the salts will precipitate; before use, warm solution until salts redissolve. Test solution for mold contamination by retaining sample of newly created solution at room temperature in an enclosed glass container. If mold is present, discard refrigerated solution.

0.05 M Phosphate buffers (1.0 Liter)
  Dilute 100 ml 0.5 M phosphate buffer to 1.0 liter with distilled water. pH 7.4.
15% PEG-0.001% Triton (1.0 Liter)
  150 grams polyethyleneglycol
  0.01 gram Triton
  Dissolve and dilute to 1.0 liter with distilled water.
Additional reagents necessary to the preferred embodiment may be based on the foregoing reagents.

PREPARATION OF CHICKEN ANTI-hPTH$^{65-84}$ REAGENT

Chicken Anti-hPTH$^{65-84}$ Reagent is the result of raising the chicken anti-hPTH$^{65-84}$ antibody against intact bovine parathyroid hormone. This antibody was chosen for its high affinity for intact hPTH, C-terminal hPTH fragments, and radioactively labeled hPTH$^{65-84}$. As alternative embodiments, other antibodies with a substantially high affinity for these three substances, could be utilized in a C-terminal PTH RIA kit. Such antibodies may be raised in animals other than chickens. Also such antibodies may be raised in chickens or other animals against substances other than intact bovine PTH. Such antibodies may be raised, for example, against intact hPTH and certain fragments of the foregoing.

The chicken anti-hPTH$^{65-84}$ antibody also has a high affinity for intact bovine PTH and bovine PTH$^{65-84}$. C-terminal fragments of bovine PTH at least as large as those fragments of bovine PTH within the range of about 65-84 are designated herein as C-terminal bovine PTH fragments. This antibody has a high affinity for such fragments. Furthermore, this antibody has a high affinity for intact rat PTH. This suggests that certain of the larger C-terminal fragments of rat PTH are sufficiently similar in structure to hPTH$^{65-84}$ that the antibody will have a high affinity for such fragments. C-terminal fragments of rat PTH at least as large as those fragments of rat PTH within the range of about 65-84 are designated herein as C-terminal rat PTH fragments. It is thought that either the chicken anti-hPTH$^{65-84}$ antibody or a substitute antibody with a high affinity for radio-activity labeled fragments within the range of about 65-84 of bovine PTH or hPTH will have a high affinity for the parathyroid hormone of any mammal. Fragments of the particular mammalian parathyroid hormone which can be measured by an RIA incorporating such antibodies are designated herein as C-terminal fragments of the particular mammalian parathyroid hormone.

To prepare Chicken Anti-hPTH$^{65-84}$ Reagent, purchase crude bovine PTH TCA powder (Inolex Corp., Glenwood, Ill. 60425) and purify it by conventional means. Dissolve 40 mg of the powder in 10 ml 0.2 M acetic acid-ammonium acetate buffer. Add to the dissolved powder both a suspension of blue dextran and a quantity of Na$^{125}$I representing approximately 100,000 cpm. Layer this mixture onto a G-75 Sephadex 60×1.5 cm fine column using downward flow and eluate with acetic acid-ammonium acetate buffer. The first peak represents the void volume as marked by the blue dextran. The second peak represents the included volume as marked by $^{125}$I. Collect eluates on a 1.25 minute basis between the void and included volume and assay each tube to confirm the presence of purified labeled bPTH. Pool tubes containing immunoreactive bovine PTH and assay pooled material to determine the quantity thereof.

Inject 0.1 mg of the purified labeled bovine PTH emulsified with an equal volume of Freund's complete adjuvant, weekly for four weeks, in four sites near wings and legs on the underside of the boides of Rhode Island or Leghorn Red chickens. In the fifth week, bleed the chickens from a vein under the wing and test for good titer.

Centrifuge the chicken's blood to isolate the plasma. Titer the plasma against $^{125}$I-Tyr$^{64}$-hPTH$^{65-84}$. Prepared dilutions of 1/500, 1/1,000, 1/5,000, 1/10,000, 1/20,000, and 1/30,000 by volume, by adding appropriate quantities of 1% BSA-0.1 M borate buffer to the isolated chicken plasma. Add to 200 μl of each dilution of chicken plasma 200 μl of $^{125}$I-Tyr$^{65-84}$ Reagent (cf. preparation of $^{125}$I-Tyr$^{65-84}$ Reagent infra). Vortex gently and incubate for 24 hours at 2°-8° C. Follow the protocol (cf. protocol infra) beginning with the addition of RAC-PPT Reagent (cf. preparation of RAC-PPT Reagent infra). Plot percent binding of the chicken antibody to $^{125}$I-Tyr$^{64}$-hPTH$^{65-84}$ against dilution of the chicken plasma according to the counts registered for precipitated and non-precipitated $^{125}$I-Tyr$^{64}$-hPTH$^{65-84}$. Good titer is represented by the dilution which has at least 40–50% binding.

Bleed the animal weekly if good titer is present. Maintain animal thereafter by injecting 0.05 mg of the purified labeled bovine PTH emulsified with an equal volume of Freund's complete adjuvant.

Substantially maximal sensitivity of the assay kit, on the order of 0.2 ng/ml hPTH$^{1-84}$ equivalents, is achieved by maintaining a pool of chicken anti-hPTH$^{65-84}$ plasma solution for which there is approximately 40–50% binding. The pool is maintained by adding to it chicken anti-hPTH$^{65-84}$ plasma at a concentration in 1% BSA-0.1 M borate buffer which according to its titer will result in 40–50% binding.

In the case of the presently existing pool, Chicken Anti-hPTH$^{65-84}$ Reagent is prepared by diluting 1.0 ml of the pooled plasma solution to 100 ml with 1% BSA-0.1 M borate buffer. One ml of the 1/100 dilution is diluted to 48 ml with 1% BSA-0.1 M borate buffer. Five ml of the 1/4,800 dilution is aliquoted per 30 ml Wheaton vial, lyophilized, and stored at −20° C. Add 25 ml of distilled water to reconstitute for use as Chicken Anti-hPTH$^{65-84}$ Reagent.

PREPARATION OF RABBIT ANTI-CHICKEN PRECIPITATING COMPLEX REAGENT

Rabbit Anti-Chicken Precipitation Complex Reagent (RAC-PPT Reagent) is the result of raising a rabbit antibody against the gamma globulin of chickens. This particular rabbit antibody was chosen for its high affinity for chicken anti-hPTH$^{65-84}$. The rabbit antibody is added to polyethylene glycol (PEG) and normal chicken serum (NCS) to form a pre-precipitated accelerated precipitating complex.

As alternative embodiments, other antibodies with a substantially similar affinity for chicken anti-hPTH$^{65-84}$ may be utilized in a C-terminal PTH RIA kit. Such antibodies may be raised in animals other than rabbits. Also such antibodies may be raised in rabbits and other animals against substances other than this particular chicken gamma globulin, such as whole chicken serum or plasma.

To prepare the RAC-PPT Reagent, separate gamma globulin from the chicken plasma for which there was good titer against $^{125}$I-Tyr$^{64}$-hPTH$^{65-84}$ by the conventional method of salting out with $33\frac{1}{3}\%$ saturated $(NH_4)_2SO_4$. Inject 1.0 mg of the gamma globulin emulsified with an equal volume of Freund's complete adjuvant, weekly for four weeks, in four sites near the legs on the underside of New Zealand White rabbits. In the fifth week, bleed each rabbit from a vein under a leg and test the titer.

Centrifuge the rabbit's blood to isolate the plasma. To find the concentration or titer of rabbit antibody, prepare dilutions of $\frac{1}{2}$, $\frac{1}{3}$, $\frac{1}{4}$, 1/5, 1/7.5, 1/10, 1/15, 1/20, 1/25, 1/30, and 1/50 by volume, by adding appropriate quantities of 1% BSA-0.10 M borate buffer to the isolated rabbit plasma. To reaction vessels corresponding to each dilution, add 200 μl of Chicken Anti-hPTH$^{65-84}$ Reagent to 200 μl of $^{125}$I-Tyr$^{64}$-hPTH$^{65-84}$ Reagent. Vortex gently and incubate 20 hours at 2°–8° C. To each of the reaction vessels, add 200 μl of 1/200 normal chicken serum (NCS does not contain the chicken anti-hPTH$^{65-84}$ antibody), 200 μl of 15% PEG-0.001% Triton, and 200 μl of one of the dilutions of the rabbit plasma. Vortex gently and incubate for exactly two hours at 2°–8° C. Follow the protocol infra from thereon.

Plot the ratio of the cpm of the precipitate to total cpm of precipitate and supernatant against the dilution of rabbit plasma. Maximal binding of the rabbit antibody to chicken anti-hPTH$^{65-84}$ occurs at the concentration of rabbit plasma for which the ratio of cpm's is greatest. This concentration is defined as the working concentration or titer of the rabbit antibody.

Bleed the animal weekly if good titer is present. Maintain animal thereafter by injecting 0.5 mg of the chicken gamma globulin emulsified with an equal volume of Freund's complete adjuvant.

To prepare RAC-PPT Reagent, mix equal volumes of NCS at 1/40 dilution in 5% BSA-0.25 M borate buffer and rabbit plasma at five times the working concentration diluted with 5% BSA-0.25 M borate buffer. Mix well and aliquot 12 ml per 100 ml vial. Add 22.5 ml of 15% PEG-0.001% Triton to each vial. Lyophilize and store at −20° C. Add 100 ml of distilled water to reconstitute for use as RAC-PPT Reagent.

PREPARATION OF $^{125}$I-Tyr$^{64}$-hPTH$^{65-84}$ REAGENT

The $^{125}$I-Tyr$^{64}$-hPTH$^{65-84}$ Reagent is the result of three principal steps: (1) synthesizing Tyr$^{64}$-hPTH$^{65-84}$; (2) labeling the synthesized compound with $^{125}$I; and (3) dissolving the labeled compound in an appropriate buffer at an appropriate concentration.

As alternative embodiments, the hPTH$^{65-84}$ fragment may be labeled radioactively in many conventional ways, including but not limited to, attaching histidyl, tyramyl, histamyl, or other similar substances to the fragment and labeling with radioiodine. As an alternative to $^{125}$I, $^{131}$I may be used. As a further alternative embodiment, a radioactively labeled fragment within the range of about 65–84 of bovine PTH or hPTH could be substituted for the radioactively labeled hPTH$^{65-84}$.

1. Synthesizing Tyr$^{64}$-hPTH$^{65-84}$

The compound Tyr$^{64}$-hPTH$^{65-84}$ consists of the following: NH$_2$-Tyr-Lys-Ser-Leu-Gly-Glu-Ala-Asp-Lys-Ala-Asp-Val-Asp-Val-Leu-Thr-Lys-Ala-Lys-Ser-Gln-COOH.

Tyr$^{64}$-hPTH$^{64-84}$ is synthesized by solid state peptide synthesis, a method discovered by R. B. Merrifield and detailed in Stewart & Young, *Solid State Peptide Synthesis* (W. F. Freeman & Co. 1969).

The Synthesis proceeds from the carboxyl end of hPTH sequence, adding one amino acid per cycle of reaction. In general, each amino acid to be added is protected by BOC (tertiary butyloxycarbonyl) at its carboxyl end. The peptide chain is linked by its carboxyl end to DVB resin (a copolymer of styrene and divinyl benzene). The starting material, BOC-Gln-DVB resin, is available commercially (Peninsula Laboratories, Inc., Belmont, Calif. 94002). Place 1.0 mM (i.e. 2.0 gm) BOC-Gln-DVB resin in a reaction vessel. The BOC group is cleaved from the Gln-DVB resin by a surplus (hereinafter a quantity sufficient to cover the resin in the reaction vessel) of 40% solution by volume of trifluoro acetic acid in $CH_2Cl_2$. Stir for 20 minutes and drain. The reaction vessel and contents should be at room temperature for this and all succeeding steps in the synthesis. Then wash with a surplus of pure $CH_2Cl_2$, stir and drain. The Gln-DVB resin is neutralized by adding 20 ml of 10% solution by volume of triethyamine in $CH_2Cl_2$. Stir for 10 minutes and drain. Then wash with a surplus of pure $CH_2Cl_2$, stir and drain. Repeat washing twice with fresh $CH_2Cl_2$.

In the next cycle, add 5 molar equivalents (defined according to the Gln-DVB resin) of the next amino acid in the hPTH$^{65-84}$ sequence. In this particular cycle, the compound added would be BOC-Ser-Bzl (Benzyl group). Certain amino acids, such as Ser, Lys, Thr, Asp, Glu, and Tyr, require side chain protection to ensure that the amino acid remains intact throughout the synthesis. This is accomplished by employing BOC-Ser-Bzl rather than BOC-Ser in the initial step of the Ser cycle. Similarly, BOC-Lys-Cl-Z (Chlorocarbobenzosy), BOC-Thr-Bzl, BOC-Glu-Bzl, and BOC-Tyr-Br-Z (Bromocarbobenzosy) are substituted in the reaction for the unprotected BOC-amino acid. No protection is required for Ala, Leu, Val, and Gly. The above mentioned unprotected and protected BOC-amino acids are available commercially (Peninsula Laboratories, Inc., Belmont, Calif. 94002). For alternative embodiments, BOC-histamyl, BOC-histidyl, and BOC-tyramyl, along with appropriate side chain protection, are available commercially (Peninsula).

To the Gln-DVB resin and the BOC-Ser-Bz, add 5 molar equivalents of dichlorohexycarbodiamide dissolved in a surplus of $CH_2Cl_2$. Stir for 2 hours. Apply ninhydrin test. If the test yields negative results, the reaction is complete and the contents of the reaction vessel should be washed three times with a surplus of $CH_2Cl_2$. If the test yields a positive result, the reaction should be continued until complete. After washing, the BOC group is cleaved and the peptide-resin is neutralized by the steps set forth above. The cycle is repeated with an appropriate protected or unprotected BOC-amino acid until Tyr$^{64}$-hPTH$^{65-84}$-DVB resin, or the appropriate alternative embodiment, is the result.

The completed peptide, Tyr$^{64}$-hPTH$^{65-84}$, is cleaved from the DVB resin and the side protecting groups are stripped off the protected amino acid by washing the contents of the reaction vessel with 20 ml of anhydrous HF. The peptide is purified by countercurrent exchange using butanol-acetic acid-water in the ratio of 4:1:5. The purity of the peptide can be confirmed by thin layer countercurrent chromatography and HPLC.

2. Labeling $Tyr^{64}$-$hPTH^{65-84}$

The preferred labeling material is $^{125}I$, although other materials could be used. The labeling procedure stems from Yalow and Berson, 212 *Nature* 357 (1966) and Hunter & Greenwood, 194 *Nature* 495 (1962). $Na^{125}I$ in a standard NaOH solution is manufactured weekly by Amersham Searle (Arlington Heights, Ill. 60005). $Na^{125}I$ that is older than two weeks should not be used. Chloramine T is manufactured by Matheson, Coleman and Bell (Cincinnati, Ohio 45212). The stability of Chloramine T is unknown. Chloramine T older than six months should not be used. Sodium metabisulfite is commonly available.

Sephadex G-100, fine grade 40-20 microparticle diameter, should be utilized in the labeling procedure. A 60×1 cm column at room temperature should be packed in a level position. The Sephadex slurry is poured down a glass rod into the column. After the column is poured, add 4 ml of 5% BSA-0.1 M borate buffer and approximately 0.5 ml of 0.5% blue dextran. Run two volumes of 0.1 M borate buffer through the column to pack it thoroughly and to wash excess BSA off the column. The blue dextran checks column packing and determines void volume. To achieve this, the eluate is collected into a graduated cylinder beginning with the addition of the blue dextran until the blue dextran comes off the column.

Pick a gamma counter with linear response in the range of 50,000 to 200,000 cpm (Tracor Analytic, Elk Grove Village, Ill. 60007). Place a two millicurie sample of $Na^{125}I$ in the standard NaOH solution in a V-vial. Adjust the gamma counter so that the counts are kept between 50,000 and 200,000 cpm by adjusting the distance of V-vial from the gamma counter, the geometry of the well of the counter, and the gamma counter's window. Add 50 $\mu l$ of 0.5 M phosphate buffer to the V-vial. The strong buffer is necessary to neutralize the NaOH. Cover tightly and vortex until the meniscus disappears. Add 60 $\mu l$ of 0.1 $\mu g/\mu l$ of $Tyr^{64}$-$hPTH^{65-84}$ in 0.1 N acetic acid by placing the pipet tip containing that solution below the meniscus in the V-vial and very gently blowing. After ten seconds, add 10 $\mu l$ of Chloramine T solution by similarly gently blowing it below the meniscus. Cover tightly and mix. The Chloramine T solution should be prepared within 1 hour of its use by diluting 12.5 mg of Chloramine T to a volume of 10.0 ml with 0.05 M phosphate buffer. After mixing the contents of the V-vial for 30 seconds, add 25.0 $\mu l$ of sodium metabisulfite solution below the meniscus and vortex. The sodium metabisulfite solution is made by diluting 12.5 mg of sodium metabisulfite to a volume of 10.0 ml with 0.05 M phosphate buffer. Transfer the V-vial's contents to the top of the dry Sephadex bed with a Pasteur pipet that was rinsed with 5% BSA-0.1 M borate buffer. The latter helps prevent labeled $Tyr^{64}$-$hPTH^{65-84}$ from sticking to the pipet. Allow the V-vial's contents to soak into the bed. Rinse vial with 200 $\mu l$ of 5% BSA-0.25 M borate buffer by repeatedly washing down sides of V-vial with the same BSA. Transfer the 200 $\mu l$ wash to the column with the same Pasteur pipet. Allow to soak into bed. Operate the fraction collector manually during sample and rinse application. Rinse sides of column with a small amount of 0.1 M borate buffer (usually 0.25-0.5 ml) and allow it to soak into the bed. Fill the area of column above the bed with 0.1 M borate buffer and attach reservoir. With a fraction collector, collect 0.5 ml eluates per 1.25 minutes. Collect approximately 100 fractions.

Count V-vial in which labeling reaction took place and count each eluate. Plot eluate counts on plain graph paper with counts on the ordinate and eluate number on the abscissa. The first peak is generally considered damaged PTH fragment and is discarded. The third peak represents free salt. The second peak is the good labeled hormone and is saved and pooled into a plastic bottle using a Pasteur pipet to transfer the solution. Use 20 ml minus the estimated volume of the pooled eluate of 5% BSA-0.25 M borate buffer for rinsing the eluate tubes and the Pasteur pipet. Mix the pooled eluates, and any unused 5% BSA-0.25 M borate buffer.

After plotting the eluate counts against the eluate number, separate the protein counts (first two peaks) from free salt (the third peak). The percent transfer may be calculated by the formula:

$$\% \text{ Transfer} = 100 \times \frac{\text{protein associated counts}}{\text{protein associated counts} + \text{free salt counts}}$$

The specific activity may be calculated by the formula:

$$\text{Specific activity} = \% \text{ Transfer} \times \frac{\mu c \text{ of } ^{125}I}{\mu g \text{ of protein}}$$

A specific activity within the range of 100-200 $\mu c/\mu g$ is acceptable. A count of the reaction vial should not yield a result that is more than 5% the total counts of the original vial and contents. If the count exceeds 5%, the number in excess of 5% should be considered to be protein associated and therefore must be deducted from the amount of protein applied to the column. The amount of protein applied to the column may be calculated by the formula:

$$\text{Am't protein applied} = \text{am't protein added} \times \left[ 1 - \frac{\text{counts of protein sticking to vial}}{\text{total counts of original vial}} \right]$$
to reaction vial The amount of labeled protein per container may be calculated by the formula:

$$\text{Am't labeled protein per container} = \text{total am't protein applied} \times \frac{\text{counts per container}}{\text{total protein associated counts}}$$

3. $^{125}I$-$Tyr^{64}$-$hPTH^{65-84}$ Reagent

Dilute the pooled eluate representing the second peak to a sufficient volume with 5% BSA-0.25 M borate buffer in 0.22 M EDTA so that the concentration of $^{125}I$-$Tyr^{64}$-$hPTH^{65-84}$ is 1.25 nanograms/ml based on the preceding formula for calculating the amount of labeled protein per container. Aliquot 5 ml of $^{125}I$-$Tyr^{64}$-$hPTH^{65-84}$ at a concentration of 1.25 nanograms/ml into 30 ml serum vials. Store this solution at $-20°$ C. until it is lyophilized. Store at $-20°$ C. after lyophilization. The lyophilized $^{125}I$-$Tyr^{64}$-$hPTH^{65-84}$ stored at $-20°$ C. has a useful life of 6 weeks. Reconstitute the lyophilized $^{125}I$-$Tyr^{64}$-$hPTH^{65-84}$ with 25 ml of distilled water as $^{125}I$-$Tyr^{64}$-$hPTH^{65-84}$ Reagent. Perform a check on the labeling procedure by directing an assay incorporating the newly prepared $^{125}I$-$Tyr^{64}$-$hPTH^{65-84}$ Reagent against known amounts of $Tyr^{64}$-$hPTH^{65-84}$.

PREPARATION OF CONTROLS AND STANDARDS

Prepare the Normal Control Reagent from plasma units available commercially. Centrifuge to remove fibrin or filter through glass wool. Mix pool well and aliquot 2.0 ml into a 5 ml Wheaton vial using a sufficiently accurate pipetting device. Assay to determine ng/ml of $hPTH^{1-84}$ equivalents. Store at $-20°$ C. until lyophilized, and store at $-20°$ C. thereafter. Reconstitute with 2.0 ml of distilled water as Normal Control Reagent.

Prepare the High Control Reagent from plasma units available commercially. Centrifuge as indicated above. Add 1000 ng of bovine PTH to 1000 ml of pooled plasma, mix well. Assay to determine ng/ml of $hPTH^{1-84}$ equivalents. Aliquot 2.0 ml into 5 ml Wheaton vials using sufficiently accurate pipetting device. Store at $-20°$ C. thereafter. Reconstitute with 2.0 ml of distilled water as High Control Reagent.

Prepare the Zero Standard and the Nonspecific Binding Standard Reagent (NSB Reagent) by placing 8.0 ml of freshly prepared 1% BSA-0.25 M borate buffer into each of two vials, lyophilize, and store at $-20°$ C. Reconstitute each with 20 ml of distilled water as Zero Standard Reagent and as NSB Reagent respectively.

Prepare Standard Reagents of 0.312, 0.625, 1.25, 2.5, 5.0, and 10.0 ng/ml of $hPTH^{1-84}$ equivalents as follows. Dissolve and dilute 0.5 mg $Tyr^{64}$-$hPTH^{65-84}$ to 5.0 ml with 0.1 N acetic acid. One hundred $\mu l$ of this solution is further diluted to 100 ml with 1% BSA-0.1 M borate buffer. This results in a 100 ng/ml concentration of $Tyr^{64}$-$hPTH^{65-84}$. Dilute 1.0 ml of this solution with 39.0 ml of 1% BSA-0.1 M borate buffer to achieve a working dilution of 2.5 ng/ml which is equal to 10.0 ng/ml of $hPTH^{1-84}$ equivalents. Serially dilute the 10.0 ng/ml of $hPTH^{1-84}$ equivalents standard with 1% BSA-0.1 M borate buffer to give 5, 2.50, 1.25, 0.625, and 0.312 ng/ml of $hPTH^{1-84}$ equivalents standards. Aliquot 500 $\mu l$ of each standard in 2.5 ml serum vials. Dispensing volume should remain in range of $500 \pm 5.0$ $\mu l$. Store at $-20°$ C. before and after lyophilizing. Reconstitute each standard with 500 $\mu l$ of distilled water as the respective Standard Reagent.

All of the lyophilized standards have a useful life of at least one year.

PROTOCOL

1. Reconstitute lyophilized reagents as indicated.
2. Label $12 \times 75$ mm glass tubes in duplicate according to the needs of protocol. Commercially available tubes with lowest nonspecific binding are those of CMB Dispo, SP Dispo, and Kimble (Curtis Matheson Scientific, Inc., Houston, Texas 77001).
3. Add reagents to the tubes as follows:
   a. Nonspecific binding (NSB)
      250 $\mu l$ of NSB Reagent
   b. Zero standard
      50 $\mu l$ of Zero Standard Reagent.
      200 $\mu l$ of Chicken Anti-$hPTH^{65-84}$ Reagent.
   c. hPTH standards (0.312 ng/ml-10 ng/ml)
      50 $\mu l$/tube respectively of each Standard Reagent.
      200 $\mu l$ of Chicken Anti-$hPTH^{65-84}$ Reagent.
   d. Quality control
      50 $\mu l$/tube respectively of High Control and Normal Control Reagents.
      200 $\mu l$ of Chicken Anti-$hPTH^{65-84}$ Reagent.
   e. Unknown sera
      50 $\mu l$ of unknown serum
      200 $\mu l$ of Chicken Anti-$hPTH^{65-84}$ Reagent.
4. Vortex gently and incubate 4 hours at $2°-8°$ C. Incubation can be extended to 24 hours for increased sensitivity.
5. Add 200 $\mu l$ of $^{125}I$-$Tyr^{64}$-$hPTH^{65-84}$ Reagent to all tubes.
6. Vortex gently and incubate 20 hours at $2°-8°$ C.
7. Add 500 $\mu l$ of RAC-PPT Reagent.
8. Vortex gently without foaming and incubate at room temperature for a minimum of 2 hours or at $2°-8°$ C. for a minimum of 16 hours.
9. Centrifuge the tubes for 20 minutes at a minimum of $760 \times g$.
10. Decant supernatants in separate $12 \times 75$ mm tubes.
11. Count the supernatant and its related precipitate, each for a sufficient time to achieve statistical significance.

As an alternative embodiment, the above protocol may be altered so that the 200 $\mu l$ of Chicken Anti-$hPTH^{65-84}$ Reagent and 200 $\mu l$ of $^{125}I$-$Tyr^{64}$-$hPTH^{65-84}$ Reagent are added as one step to the NSB Reagent, various standard reagents, control reagents, and unknown serum. This initial step may be followed by vortexing gently and incubating for 16 hours at $2°-8°$ C. However, greater assay sensitivity is generally obtained by the order of reactions indicated by the preferred embodiment.

RESULTS

Figure 1:
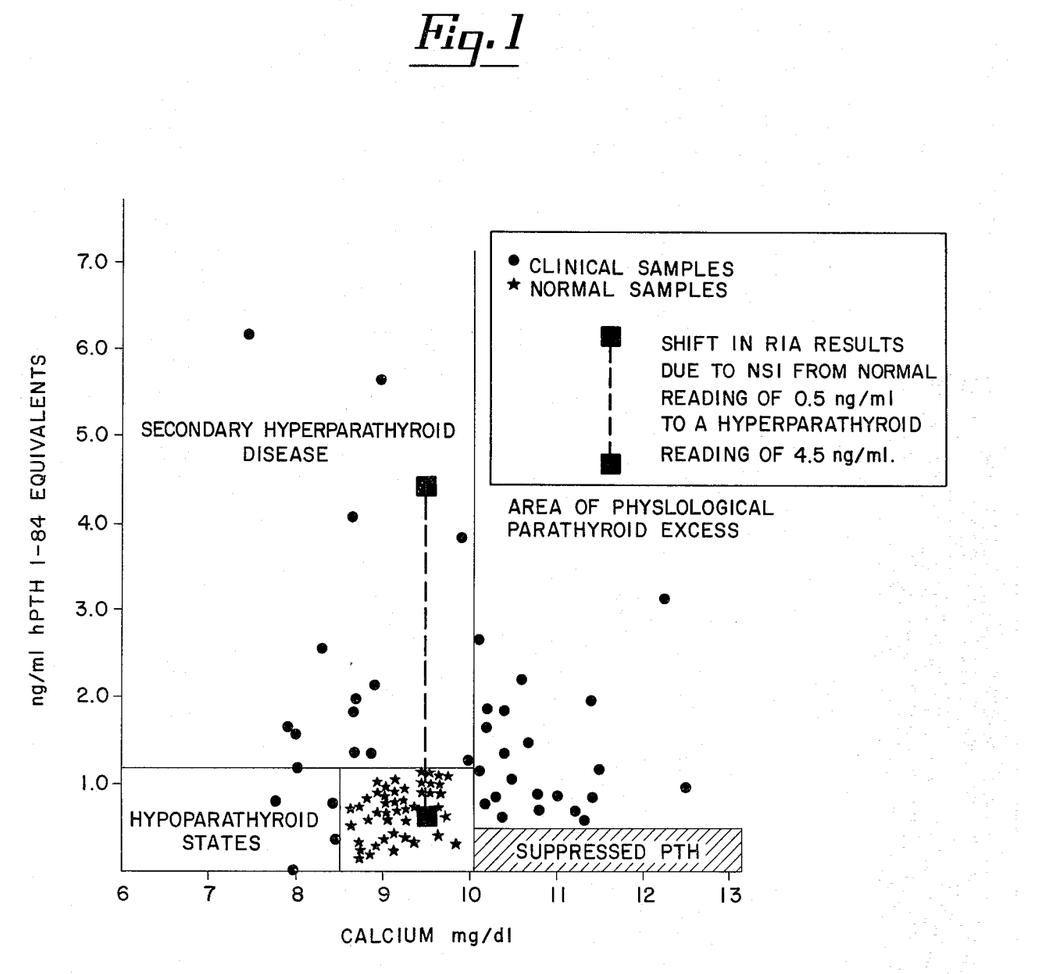
FIG. 1 illustrates that spurious assay results due to NSI can result in mischaracterizing normal human serum as being indicative of hyperparathyroidism.
Figure 2:
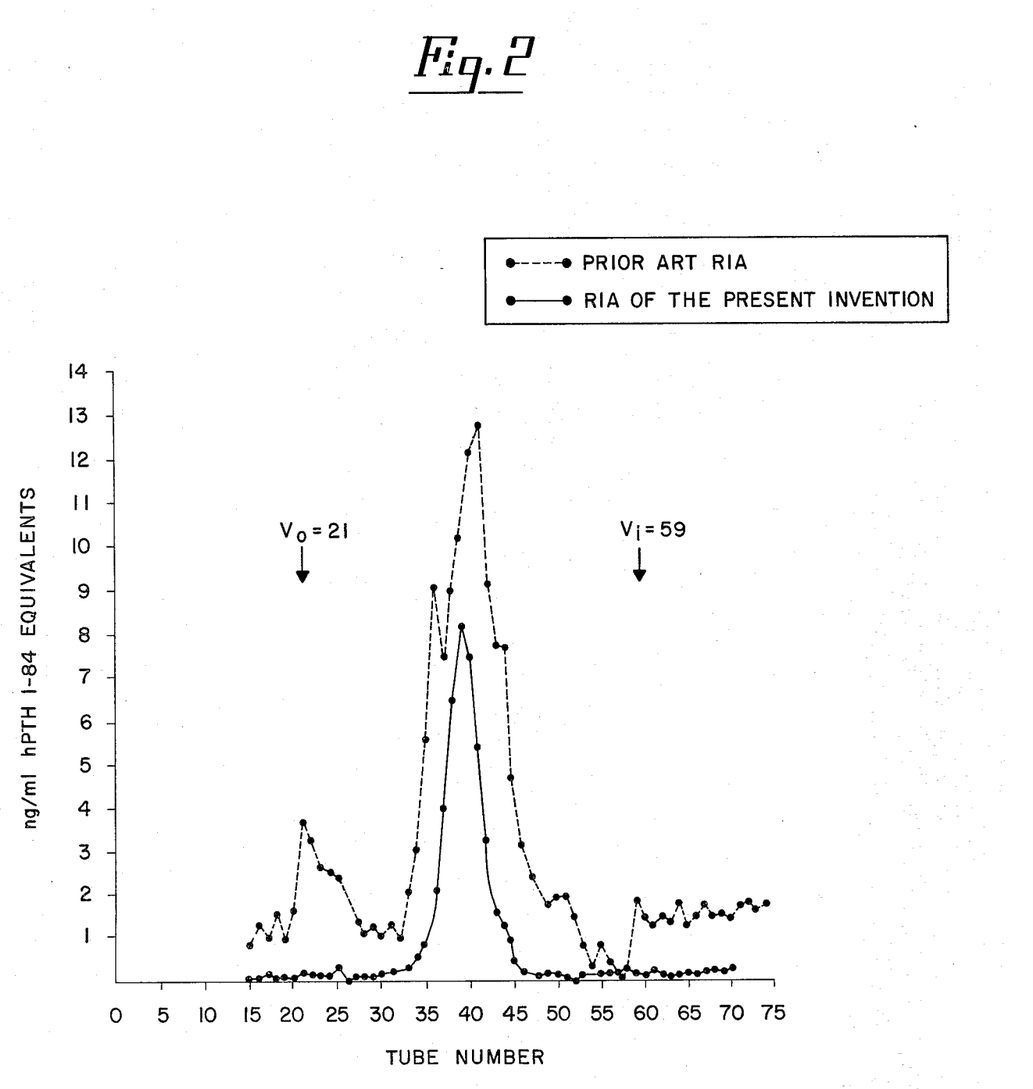
FIG. 2 illustrates that the RIA of the present invention eliminates NSI by comparing the results of this RIA with a prior art RIA where the assays are directed to the void volume of chromatographically separated serum.
Figure 3:
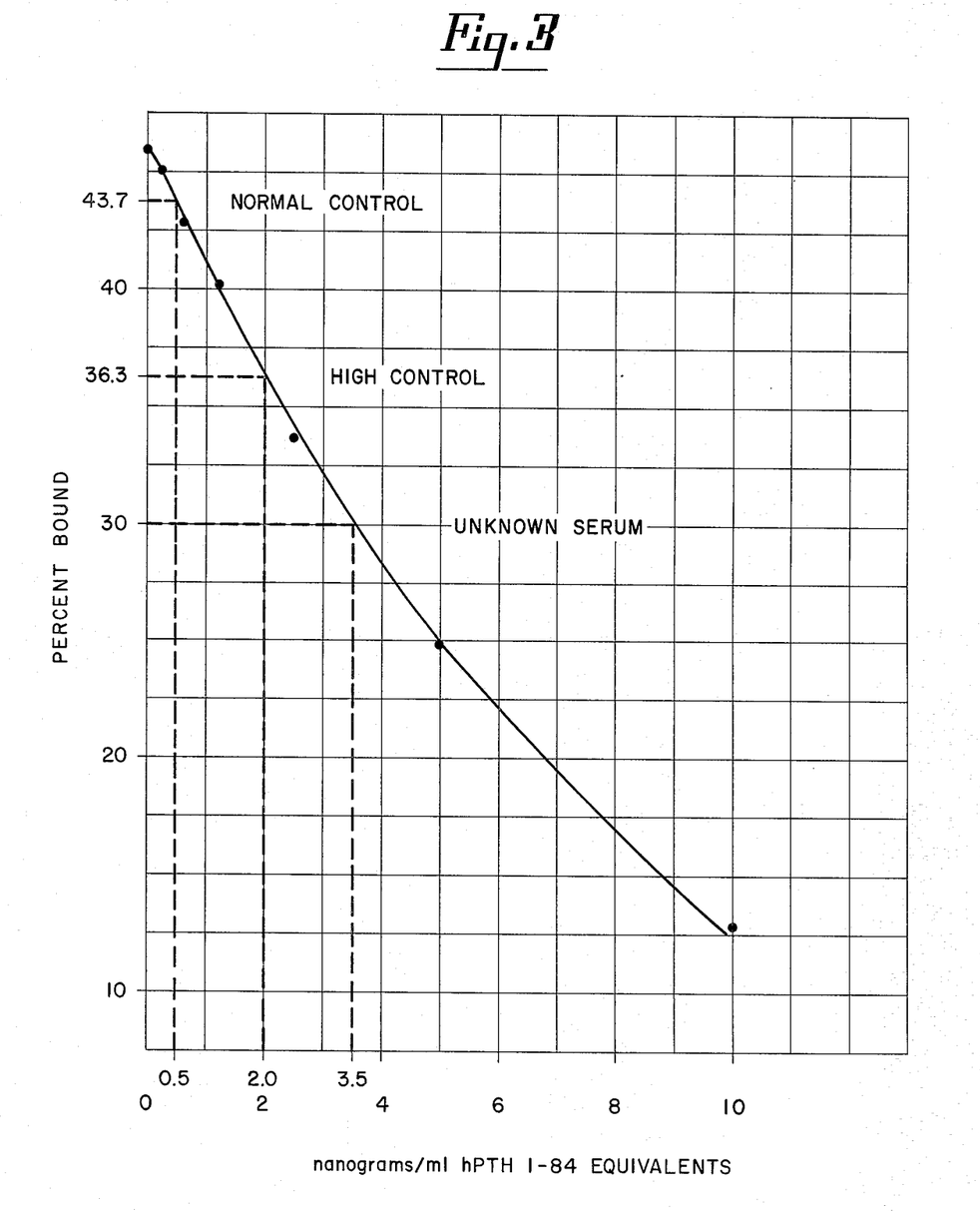
FIG. 3 is a standard curve plotting % binding vs. concentration.

The concentration of intact hPTH and C-terminal hPTH fragments in the unknown human serum are determined by reference to a standard curve. Standard curves may be obtained by several methods, for example, by plotting percent binding vs. concentration or by plotting cpm of precipitate, or the supernatant, or the ratio therebetween vs. concentration. FIG. 3 shows a sample standard curve where percent binding is plotted vs. concentration in ng/ml of $hPTH^{1-84}$ equivalents. The percent binding may be calculated by the formula:

$$\% \text{ Binding} = \frac{cpm \text{ sample precipitate} - cpm \text{ NSB precipitate}}{cpm \text{ zero standard precipitate} - cpm \text{ NSB precipitate}}$$

As an alternative embodiment, the results of the nonspecific binding (NSB) sample may be incorporated in the calculation of the percent binding. NSB, not to be confused with NSI, is the result of radioactive supernatant residing in the precipitate and protein binding to the walls of the assay tubes, as well as other factors. An alternative calculation should be used when the NSB sample results in precipitate cpm's indicating greater than 5% binding. The % binding for a sample may be calculated in the alternative by the formula:

$$\% \text{ Binding} = 100 \times \frac{cpm \text{ for precipitate}}{\text{total } cpm \text{ for precipitate \& supernatant}}$$

The alternative calculation of % binding is used for % binding of NSB samples that exceed 5%. For binding of NSB samples of 5% or less, the distortion due to NSB is thought to be substantially uniform for all samples. The RIA's based on the foregoing protocol typically result in 5% binding for NSB samples.

Figure 4:
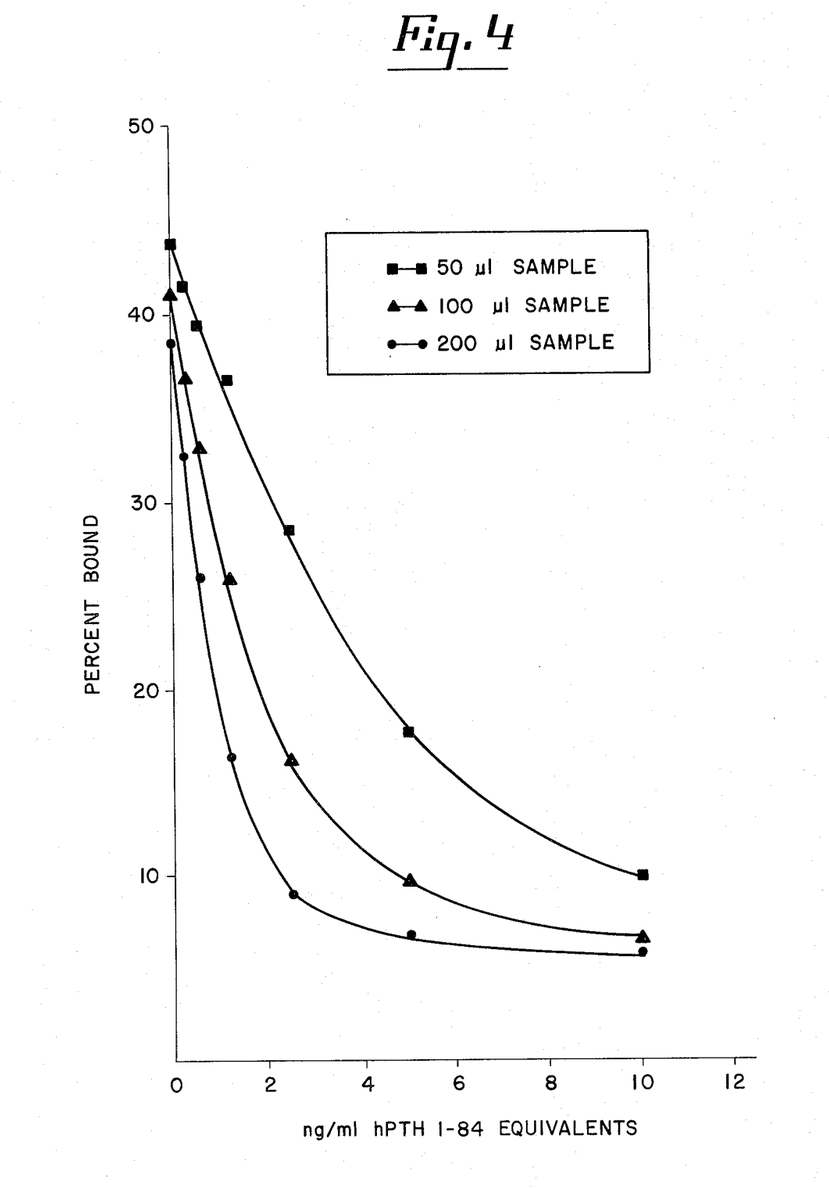
FIG. 4 is a comparison of standard curves for 50, 100, and 200 μl of standard and unknown serum.

As another alternative embodiment, the assay may be run with 100 or 200 μl of standards and unknown serum for greater sensitivity at low concentrations. FIG. 4 compares standard curves for 50, 100, and 200 μl of standard and unknown serum. Conversely, if the concentration of an unknown serum sample exceeds 10 ng/ml, a second assay of the serum pool diluted by 0.4% BSA-0.1 M borate buffer will yield the concentration after applying an appropriate dilution factor.

Data for the purposes of illustration are shown below. These numbers were used to plot the standard curve in FIG. 3 which results in a concentration of 3.5 ng/ml of hPTH$^{1-84}$ equivalents for the unknown serum sample.

| Sample | Average (2 tubes) cpm of supernatant | Average (2 tubes) cpm of precipitate | % binding | Known ng/ml hPTH$^{1-84}$ equivalents | Calculated ng/ml hPTH$^{1-84}$ equivalents |
|---|---|---|---|---|---|
| NSB | 14,265 | 735 | 4.9% | — | — |
| Standard | 8,100 | 6,900 | 46.0% | 0 | — |
|  | 8,175 | 6,825 | 45.5% | 0.312 | — |
|  | 8,550 | 6,450 | 43.0% | 0.625 | — |
|  | 9,000 | 6,000 | 40.0% | 1.25 | — |
|  | 9,945 | 5,055 | 33.7% | 2.5 | — |
|  | 11,250 | 3,750 | 25.0% | 5.0 | — |
|  | 13,125 | 1,875 | 12.5% | 10.0 | — |
| Quality Control - Normal | 8,445 | 6,555 | 43.7% | 0.5 | 0.5 |
| High | 9,555 | 5,445 | 36.3% | 2.0 | 2.0 |
| Unknown | 10,500 | 4,500 | 30.0% | — | 3.5 |

I claim:

1. A method of double antibody radioimmunoassay measurement of the concentration in biological or other fluids of mammalian parathyroid hormone and/or C-terminal fragments thereof which comprises incorporating in the assay as the radioactively labeled peptide a radioactively labeled fragment within the range of about 65–84 of bovine PTH or hPTH.

2. The method of claim 1 wherein the mammalian parathyroid hormone and/or C-terminal fragments thereof are respective members of the group consisting of intact rat PTH and C-terminal rat PTH fragments, intact bovine PTH and C-terminal bovine PTH fragments, and intact hPTH and C-terminal hPTH fragments.

3. The method of claim 2 wherein said respective members are intact hPTH and C-terminal hPTH fragments.

4. The method of claim 3 wherein said double antibody radioimmunoassay comprises:

A. Adding together:
1. a measured quantity of the biological or other fluid to be assayed;
2. a radioactively labeled fragment within the range of about 65–84 of bovine PTH or hPTH, in sufficient quantity and of sufficient radioactivity to give a measurable counting rate of later formed precipitated second antibody bound first antibody bound radioactively labeled fragment;
3. a first antibody, which has a substantially high affinity for intact hPTH and the radioactively labeled fragment, in sufficient quantity to bind a significant quantity of the intact hPTH, the C-terminal hPTH fragments, and the radioactively labeled fragment; and
4. a first buffering agent to buffer the mixture to a pH suitable for reaction of the first antibody with intact hPTH, C-terminal hPTH fragments, and the radioactively labeled fragment;

B. Allowing reaction of the first antibody with the intact hPTH, the C-terminal hPTH fragments, and the radioactively labeled fragment to proceed substantially to equilibrium to thereby produce first antibody bound intact hPTH, first antibody bound C-terminal hPTH fragments, and first antibody bound radioactively labeled fragment;

C. Adding:
1. a second antibody-precipitating complex, wherein the second antibody has a substantially high affinity for the first antibody, as bound to the radioactively labeled fragment, in a sufficient quantity to give a measurable counting rate of precipitated second antibody bound first antibody bound radioactively labeled fragment; and
2. a second buffering agent to buffer the mixture to a pH suitable for reaction of the second antibody with first antibody bound radioactively labeled fragment;

D. Allowing reaction of the second antibody-precipitating complex with the first antibody bound radioactively labeled fragment to proceed substantially to equilibrium to thereby produce precipitated second antibody bound first antibody bound radioactively labeled fragment;

E. Separating the precipitated from non-precipitated radioactively labeled fragment;

F. Measuring the radioactivity of the precipitated and/or non-precipitated radioactively labeled fragment;

G. Correlating the respective measured radioactivity of the precipitated and/or non-precipitated radioactively labeled fragment for the biological or other fluid with that for known standards.

5. The method of claim 4 wherein the biological or other fluid is human serum or plasma.

6. The method of claim 4 wherein precipitated is separated from non-precipitated radioactively labeled fragment by centrifuging until the supernatant is substantially clear of the precipitate, and decanting the supernatant.

7. The method of claim 4 wherein the reaction of the first antibody with intact hPTH, C-terminal hPTH fragments, and radioactively labeled fragment is allowed to proceed in the aforesaid manner by vortexing gently and incubating the vortexed material until the reaction proceeds substantially to equilibrium.

8. The method of claim 4 wherein the reaction of the second antibody-precipitating complex with the first antibody bound radioactively labeled fragment is allowed to proceed in the aforesaid manner by vortexing gently and incubating the vortexed material until the reaction proceeds substantially to equilibrium.

9. The method of claim 4 wherein said correlation comprises:

A. Preparing a standard curve for which known standards are plotted respectively against the measured radioactivity of their precipitated and/or non-precipitated radioactively labeled fragment; and B. Correlating via the standard curve the quantity of intact hPTH and C-terminal hPTH fragments in the biological or other fluid with the measured radioactivity of its precipitated and/or non-precipitated radioactively labeled fragment.

10. The method of claim 4 wherein the radioactively labeled fragment within the range of about 65–84 of bovine PTH or hPTH comprises the fragment bound at the end opposite the carboxyl group by a member of the group consisting of radioiodinated histidyl, radioiodinated tyramyl, radioiodinated histamyl, and radioiodinated tyrosyl.

11. The method of claim 10 wherein the radioiodine is $^{125}I$.

12. The method of claim 10 wherein the fragment bound by said member is hPTH$^{65-84}$.

13. The method of claim 12 wherein the radioactively labeled fragment is $^{125}I$-Tyr$^{64}$-hPTH$^{65-84}$.

14. The method of claim 12 wherein the first antibody is chicken anti-hPTH$^{65-84}$ and the first buffering agent buffers the mixture to a pH in the range of about 7.5–8.6.

15. The method of claim 14 wherein the first buffering agent comprises a borate buffer with a pH of about 8.4.

16. The method of claim 14 wherein the first buffering agent comprises a BSA-borate buffer with a pH of about 8.4.

17. The method of claim 14 wherein the reaction of chicken anti-hPTH$^{65-84}$ with intact hPTH, C-terminal hPTH fragments, and said radioactively labeled hPTH$^{65-84}$ is allowed to proceed in the aforesaid manner by vortexing gently and incubating for 16 hours at 2°–8° C.

18. The method of claim 14 wherein the second antibody-precipitating complex is rabbit anti-chicken precipitating (RAC-PPT) complex and the second buffering agent buffers the mixture to a pH in the range of about 7.5–8.6.

19. The method of claim 18 wherein the second buffering agent comprises a borate buffer with a pH of about 8.4.

20. The method of claim 18 wherein the second buffering agent comprises BSA-borate buffer with a pH of about 8.4.

21. The method of claim 18 wherein the reaction of RAC-PPT complex with the chicken anti-hPTH$^{65-84}$ bound radioactively labeled hPTH$^{65-84}$ is allowed to proceed in the aforesaid manner by vortexing and incubating for a minimum of 2 hours at room temperature or greater than 16 hours at 2°–8° C.

22. The method of claim 3 wherein said double antibody radioimmunoassay comprises:
A. Adding, to a measured quantity of the biological or other fluid to be assayed:
1. a first antibody, which has a substantially high affinity for intact hPTH, C-terminal hPTH fragments, and later to be added radioactively labeled fragment, in a sufficient quantity to bind a significant quantity of the intact hPTH and C-terminal hPTH fragments in the biological or other fluid; and
2. a first buffering agent to buffer the mixture to a pH suitable for reaction of the first antibody with intact hPTH, C-terminal hPTH fragments, and later to be added radioactively labeled fragment;
B. Allowing reaction of the intact hPTH and C-terminal hPTH fragments with the first antibody to proceed substantially to equilibrium to thereby produce first antibody bound intact hPTH and first antibody bound C-terminal hPTH fragments;
C. Adding a radioactively labeled fragment within the range of about 65–84 of bovine PTH or hPTH, in sufficient quantity to give a measurable counting rate of later formed precipitated second antibody bound first antibody bound radioactively labeled fragment;
D. Allowing reaction of the radioactively labeled fragment with the first antibody bound intact hPTH and first antibody bound C-terminal hPTH fragments to proceed substantially to equilibrium to thereby bind a portion of the radioactively labeled fragment while freeing a portion of the bound intact hPTH and C-terminal hPTH fragments;
E. Adding:
1. a second antibody-precipitating complex, wherein the second antibody has a substantially high affinity for the first antibody, as bound to the radioactively labeled fragment, in a sufficient quantity to give a measurable counting rate of precipitated second antibody bound first antibody bound radioactively labeled fragment; and
2. a second buffering agent to buffer the mixture to a pH suitable for reaction of the second antibody with first antibody bound radioactively labeled fragment;
F. Allowing reaction of the second antibody-precipitating complex with the first antibody bound radioactively labeled fragment to proceed substantially to equilibrium to thereby produce precipitated second antibody bound first antibody bound radioactively labeled fragment;
G. Separating the precipitated from non-precipitated radioactively labeled fragment;
H. Measuring the radioactivity of the precipitated and/or non-precipitated radioactively labeled fragment;
I. Correlating the respective measured radioactivity of the precipitated and/or non-precipitated radioactively labeled fragment for the biological or other fluid with that for known standards.

23. The method of claim 22 wherein the biological or other fluid is human serum or plasma.

24. The method of claim 22 wherein precipitated is separated from non-precipitated radioactively labeled fragment by centrifuging until the supernatant is substantially clear of the precipitate, and decanting the supernatant.

25. The method of claim 22 wherein the reaction of the first antibody with intact hPTH and C-terminal hPTH fragments is allowed to proceed in the aforesaid manner by vortexing gently and incubating the vortexed material until the reaction proceeds substantially to equilibrium.

26. The method of claim 22 wherein said reaction of the radioactively labeled fragment with the first antibody bound intact hPTH and first antibody bound C-terminal hPTH fragments is allowed to proceed in the aforesaid manner by vortexing gently and incubating the vortexed material until the reaction proceeds substantially to equilibrium.

27. The method of claim 22 wherein the reaction of the second antibody-precipitating complex with the first antibody bound radioactively labeled fragment is allowed to proceed in the aforesaid manner by vortexing gently and incubating the vortexed material until the reaction proceeds substantially to equilibrium.

28. The method of claim 22 wherein said correlation comprises:
   A. Preparing a standard curve for which known standards are plotted respectively against the measured radioactivity of their precipitated and/or non precipitated radioactively labeled fragment; and
   B. Correlating via the standard curve the quantity of intact hPTH and C-terminal hPTH fragments in the biological or other fluid with the measured radioactivity of its precipitated and/or non-precipitated radioactively labeled fragment.

29. The method of claim 22 wherein the radioactively labeled fragment within the range of about 65–84 of bovine PTH or hPTH comprises the fragment bound at the end opposite the carboxyl group by a member of the group consisting of radioiodinated histidyl, radioiodinated tyramyl, radioiodinated histamyl, and radioiodinated tyrosyl.

30. The method of claim 29 wherein the radioiodine is $^{125}I$.

31. The method of claim 29 wherein the fragment bound by said member is hPTH$^{65-84}$.

32. The method of claim 31 wherein the radioactively labeled fragment is $^{125}I$-Tyr$^{64}$-hPTH$^{65-84}$.

33. The method of claim 31 wherein the first antibody is chicken anti-hPTH$^{65-84}$ and the first buffering agent buffers the mixture to a pH in the range of about 7.5–8.6.

34. The method of claim 33 wherein the first buffering agent comprises a borate buffer with a pH of about 8.4.

35. The method of claim 33 wherein the first buffering agent comprises a BSA-borate buffer with a pH of about 8.4.

36. The method of claim 33 wherein the reaction of chicken anti-hPTH$^{65-84}$ with intact hPTH and C-terminal hPTH fragments is allowed to proceed in the aforesaid manner by vortexing gently and incubating for a minimum of 4 hours at 2°–8° C.

37. The method of claim 33 wherein the reaction of the radioactively labeled fragment with the first antibody bound intact hPTH and first antibody bound C-terminal hPTH fragments is allowed to proceed in the aforesaid manner by vortexing gently and incubating for at least 20 hours at 2°–8° C.

38. The method of claim 33 wherein the second antibody-precipitating complex is rabbit anti-chicken precipitating (RAC-PPT) complex and the second buffering agent buffers the mixture to a pH in the range of about 7.5–8.6.

39. The method of claim 38 wherein the second buffering agent comprises a borate buffer with a pH of about 8.4.

40. The method of claim 38 wherein the second buffering agent comprises a BSA-borate buffer with a pH of about 8.4.

41. The method of claim 38 wherein the reaction of RAC-PPT complex with the chicken anti-hPTH$^{65-84}$ bound radioactively labeled fragment is allowed to proceed in the aforesaid manner by vortexing and incubating for a minimum of 2 hours at room temperature or greater than 16 hours at 2°–8° C.

42. The method of claim 2 wherein said respective members are intact rat PTH and C-terminal rat PTH fragments.

43. The method of claim 42 wherein said double antibody radioimmunoassay comprises:

A. Adding together:
   1. a measured quantity of the biological or other fluid to be assayed;
   2. a radioactively labeled fragment within the range of about 65–84 of bovine PTH or hPTH, in sufficient quantity and of sufficient radioactivity to give a measurable counting rate of later formed precipitated second antibody bound first antibody bound radioactively labeled fragment;
   3. a first antibody, which has a substantially high affinity for intact rat PTH and the radioactively labeled fragment, in sufficient quantity to bind a significant quantity of the intact rat PTH, the C-terminal rat PTH fragments, and the radioactively labeled fragment; and
   4. a first buffering agent to buffer the mixture to a pH suitable for reaction of the first antibody with intact rat PTH, C-terminal rat PTH fragments, and the radioactively labeled fragment;
B. Allowing reaction of the first antibody with the intact rat PTH, the C-terminal rat PTH fragments, and the radioactively labeled fragment to proceed substantially to equilibrium to thereby produce first antibody bound intact rat PTH, first antibody bound C-terminal rat PTH fragments, and first antibody bound radioactively labeled fragment;
C. Adding:
   1. a second antibody-precipitating complex, wherein the second antibody has a substantially high affinity for the first antibody, as bound to the radioactively labeled fragment, in a sufficient quantity to give a measurable counting rate of precipitated second antibody bound first antibody bound radioactively labeled fragment; and
   2. a second buffering agent to buffer the mixture to a pH suitable for reaction of the second antibody with first antibody bound radioactively labeled fragment;
D. Allowing reaction of the second antibody-precipitating complex with the first antibody bound radioactively labeled fragment to proceed substantially to equilibrium to thereby produce precipitated second antibody bound first antibody bound radioactively labeled fragment;
E. Separating the precipitated from non-precipitated radioactively labeled fragment;
F. Measuring the radioactivity of the precipitated and/or non-precipitated radioactively labeled fragment; p1 G. Correlating the respective measured radioactivity of the precipitated and/or non-precipitated radioactively labeled fragment for the biological or other fluid with that for known standards.

44. The method of claim 43 wherein the biological or other fluid is rat serum or plasma.

45. The method of claim 43 wherein precipitated is separated from non-precipitated radioactively labeled fragment by centrifuging until the supernatant is substantially clear of the precipitate, and decanting the supernatant.

46. The method of claim 43 wherein the reaction of the first antibody with intact rat PTH, C-terminal rat PTH fragments, and radioactively labeled fragment is allowed to proceed in the aforesaid manner by vortexing gently and incubating the vortexed material until the reaction proceeds substantially to equilibrium.

47. The method of claim 43 wherein the reaction of the second antibody-precipitating complex with the first antibody bound radioactively labeled fragment is allowed to proceed in the aforesaid manner by vortexing gently and incubating the vortexed material until the reaction proceeds substantially to equilibrium.

48. The method of claim 43 wherein said correlation comprises:
   A. Preparing a standard curve for which known standards are plotted respectively against the measured radioactivity of this precipitated and/or non-precipitated radioactively labeled fragment; and
   B. Correlating via the standard curve the quantity of intact rat PTH and C-terminal rat PTH fragments in the biological or other fluid with the measured radioactivity of its precipitated and/or non-precipitated radioactively labeled fragment.

49. The method of claim 43 wherein the radioactively labeled fragment within the range of about 65–84 of bovine PTH or hPTH comprises the fragment bound at the end opposite the carboxyl group by a member of the group consisting of radioiodinated histidyl, radioiodinated tyramyl, radioiodinated histamyl, and radioiodinated tyrosyl.

50. The method of claim 49 wherein the radioiodine is $^{125}I$.

51. The method of claim 49 wherein the fragment bound by said member is $hPTH^{65-84}$.

52. The method of claim 51 wherein the radioactively labeled fragment is $^{125}I\text{-}Tyr^{64}\text{-}hPTH^{65-84}$.

53. The method of claim 51 wherein the first antibody is chicken anti-$hPTH^{65-84}$ and the first buffering agent buffers the mixture to a pH in the range of about 7.5–8.6.

54. The method of claim 53 wherein the first buffering agent comprises a borate buffer with a pH of about 8.4.

55. The method of claim 53 wherein the first buffering agent comprises a BSA-borate buffer with a pH of about 8.4.

56. The method of claim 53 wherein the reaction of chicken anti-$hPTH^{65-84}$ with intact rat PTH, C-terminal rat PTH fragments, and said radioactively labeled fragment is allowed to proceed in the aforesaid manner by vortexing gently and incubating for 16 hours at 2°–8° C.

57. The method of claim 53 wherein the second antibody-precipitating complex is rabbit anti-chicken precipitating (RAC-PPT) complex and the second buffering agent buffers the mixture to a pH in the range of about 7.5–8.6.

58. The method of claim 57 wherein the second buffering agent comprises a borate buffer with a pH of about 8.4.

59. The method of claim 57 wherein the second buffering agent comprises a BSA-borate buffer with a pH of about 8.4.

60. The method of claim 57 wherein the reaction of RAC-PPT complex with the chicken anti-$hPTH^{65-84}$ bound radioactively labeled $hPTH^{65-84}$ is allowed to proceed in the aforesaid manner by vortexing and incubating for a minimum of 2 hours at room temperature or greater than 16 hours at 2°–8° C.

61. The method of claim 42 wherein said double antibody radioimmunoassay comprises:
   A. Adding, to a measured quantity of the biological or other fluid to be assayed:
      1. a first antibody, which has a substantially high affinity for intact rat PTH, C-terminal rat PTH fragments, and later to be added radioactively labeled fragment, in a sufficient quantity to bind a significant quantity of the intact rat PTH and C-terminal rat PTH fragments in the biological or other fluid; and
      2. a first buffering agent to buffer the mixture to a pH suitable for reaction of the first antibody with intact rat PTH, C-terminal rat PTH fragments, and later to be added radioactively labeled fragment;
   B. Allowing reaction of the intact rat PTH and C-terminal rat PTH fragments with the first antibody to proceed substantially to equilibrium to thereby produce first antibody bound intact rat PTH and first antibody bound C-terminal rat PTH fragments;
   C. Adding a radioactively labeled fragment within the range of about 65–84 of bovine PTH or hPTH, in sufficient quantity to give a measurable counting rate of later formed precipitated second antibody bound first antibody bound radioactively labeled fragment;
   D. Allowing reaction of the radioactively labeled fragment with the first antibody bound intact rat PTH and first antibody bound C-terminal rat PTH fragments to proceed substantially to equilibrium to thereby bind a portion of the radioactively labeled fragment while freeing a portion of the bound intact rat PTH and C-terminal rat PTH fragments;
   E. Adding:
      1. a second antibody-precipitating complex, wherein the second antibody has a substantially high affinity for the first antibody, as bound to the radioactively labeled fragment, in a sufficient quantity to give a measurable counting rate of precipitated second antibody bound first antibody bound radioactively labeled fragment; and
      2. a second buffering agent to buffer the mixture to a pH suitable for reaction of the second antibody with first antibody bound radioactively labeled fragment;
   F. Allowing reaction of the second antibody-precipitating complex with the first antibody bound radioactively labeled fragment to proceed substantially to equilibrium to thereby produce precipitated second antibody bound first antibody bound radioactively labeled fragment;
   G. Separating the precipitated from non-precipitated radioactively labeled fragment;
   H. Measuring the radioactivity of the precipitated and/or non-precipitated radioactively labeled fragment;
   I. Correlating the respective measured radioactivity of the precipitated and/or non-precipitated radioactively labeled fragment for the biological or other fluid with that for known standards.

62. The method of claim 61 wherein the biological or other fluid is rat serum or plasma.

63. The method of claim 61 wherein precipitated is separated from non-precipitated radioactively labeled fragment by centrifuging until the supernatant is substantially clear of the precipitate, and decanting the supernatant.

64. The method of claim 61 wherein the reaction of the first antibody with intact rat PTH and C-terminal rat PTH fragments is allowed to proceed in the aforesaid manner by vortexing gently and incubating the vortexed material until the reaction proceeds substantially to equilibrium.

65. The method of claim 61 wherein said reaction of the radioactively labeled fragment with the first antibody bound intact rat PTH and first antibody bound C-terminal rat PTH fragments is allowed to proceed in the aforesaid manner by vortexing gently and incubating the vortexed material until the reaction proceeds substantially to equilibrium.

66. The method of claim 61 wherein the reaction of the second antibody-precipitating complex with the first antibody bound radioactively labeled fragment is allowed to proceed in the aforesaid manner by vortexing gently and incubating the vortexed material until the reaction proceeds substantially to equilibrium.

67. The method of claim 64 wherein said correlation comprises:
   A. Preparing a standard curve for which known standards are plotted respectively against the measured radioactivity of their precipitated and/or non-precipitated radioactively labeled fragment; and
   B. Correlating via the standard curve the quantity of intact rat PTH and C-terminal rat PTH fragments in the biological or other fluid with the measured radioactivity of its precipitated and/or non-precipitated radioactively labeled fragment.

68. The method of claim 61 wherein the radioactively labeled fragment within the range of about 65–84 of bovine PTH or hPTH comprises the fragment bound at the end opposite the carboxyl group by a member of the group consisting of radioiodinated histidyl, radioiodinated tyramyl, radioiodinated histamyl, and radioiodinated tyrosyl.

69. The method of claim 68 wherein the radioiodine is $^{125}I$.

70. The method of claim 68 wherein the fragment bound by said member is $hPTH^{65-84}$.

71. The method of claim 70 wherein the radioactively labeled fragment is $^{125}I\text{-}Tyr^{64}\text{-}hPTH^{65-84}$.

72. The method of claim 70 wherein the first antibody is chicken anti-$hPTH^{65-84}$ and the first buffering agent buffers the mixture to a pH in the range of about 7.5–8.6.

73. The method of claim 72 wherein the first buffering agent comprises a borate buffer with a pH of about 8.4.

74. The method of claim 72 wherein the first buffering agent comprises a BSA-borate buffer with a pH of about 8.4.

75. The method of claim 72 wherein the reaction of chicken anti-$hPTH^{65-84}$ with intact rat PTH and C-terminal rat PTH fragments is allowed to proceed in the aforesaid manner by vortexing gently and incubating for a minimum of 4 hours at 2°–8° C.

76. The method of claim 72 wherein the reaction of the radioactively labeled fragment with the first antibody bound intact rat PTH and first antibody bound C-terminal rat PTH fragments is allowed to proceed in the aforesaid manner by vortexing gently and incubating for at least 20 hours at 2°–8° C.

77. The method of claim 72 wherein the second antibody-precipitating complex is rabbit anti-chicken precipitating (RAC-PPT) complex and the second buffering agent buffers the mixture to a pH in the range of about 7.5–8.6.

78. The method of claim 77 wherein the second buffering agent comprises a borate buffer with a pH of about 8.4.

79. The method of claim 77 wherein the second buffering agent comprises a BSA-borate buffer with a pH of about 8.4.

80. The method of claim 77 wherein the reaction of RAC-PPT complex with the chicken anti-$hPTH^{65-84}$ bound radioactively labeled fragment is allowed to proceed in the aforesaid manner by vortexing and incubating for a minimum of 2 hours at room temperature or greater than 16 hours at 2°–8° C.

81. The method of claim 2 wherein said respective members are intact bovine PTH and C-terminal bovine PTH fragments.

82. The method of claim 81 wherein said double antibody radioimmunoassay comprises:
   A. Adding together:
      1. a measured quantity of the biological or other fluid to be assayed;
      2. a radioactively labeled fragment within the range of about 65–84 of bovine PTH or hPTH, in sufficient quantity and of sufficient radioactivity to give a measurable counting rate of later formed precipitated second antibody bound first antibody bound radioactively labeled fragment;
      3. a first antibody, which has a substantially high affinity for intact bovine PTH and the radioactively labeled fragment, in sufficient quantity to bind a significant quantity of the intact bovine PTH, the C-terminal bovine PTH fragments, and the radioactively labeled fragment; and
      4. a first buffering agent to buffer the mixture to a pH suitable for reaction of the first antibody with intact bovine PTH, C-terminal bovine PTH fragments, and the radioactively labeled fragment;
   B. Allowing reaction of the first antibody with the intact bovine PTH, the C-terminal bovine PTH fragments, and the radioactively labeled fragment to proceed substantially to equilibrium to thereby produce first antibody bound intact bovine PTH, first antibody bound C-terminal bovine PTH fragments, and first antibody bound radioactively labeled fragment;
   C. Adding:
      1. a second antibody-precipitating complex, wherein the second antibody has a substantially high affinity for the first antibody, as bound to the radioactively labeled fragment, in a sufficient quantity to give a measurable counting rate of precipitated second antibody bound first antibody bound radioactively labeled fragment; and
      2. a second buffering agent to buffer the mixture to a pH suitable for reaction of the second antibody with first antibody bound radioactively labeled fragment;
   D. Allowing reaction of the second antibody-precipitating complex with the first antibody bound radioactively labeled fragment to proceed substantially to equilibrium to thereby produce precipitated second antibody bound first antibody bound radioactively labeled fragment;
   E. Separating the precipitated from non-precipitated radioactively labeled fragment;
   F. Measuring the radioactivity of the precipitated and/or non-precipitated radioactively labeled fragment;
   G. Correlating the respective measured radioactivity of the precipitated and/or non-precipitated radioactively labeled fragment for the biological or other fluid with that for known standards.

83. The method of claim 82 wherein the biological or other fluid is bovine serum or plasma.

84. The method of claim 82 wherein precipitated is separated from non-precipitated radioactively labeled fragment by centrifuging until the supernatant is substantially clear of the precipitate, and decanting the supernatant.

85. The method of claim 82 wherein the reaction of the first antibody with intact bovine PTH, C-terminal bovine PTH fragments, and radioactively labeled fragment is allowed to proceed in the aforesaid manner by vortexing gently and incubating the vortexed material until the reaction proceeds substantially to equilibrium.

86. The method of claim 82 wherein the reaction of the second antibody-precipitating complex with the first antibody bound radioactively labeled fragment is allowed to proceed in the aforesaid manner by vortexing gently and incubating the vortexed material until the reaction proceeds substantially to equilibrium.

87. The method of claim 82 wherein said correlation comprises:
   A. Preparing a standard curve for which known standards are plotted respectively against the measured radioactivity of their precipitated and/or non-precipitated radioactively labeled fragment; and
   B. Correlating via the standard curve the quantity of intact bovine PTH and C-terminal bovine PTH fragments in the biological or other fluid with the measured radioactivity of its precipitated and/or non-precipitated radioactively labeled fragment.

88. The method of claim 82 wherein the radioactively labeled fragment within the range of about 65–84 of bovine PTH or hPTH comprises the fragment bound at the end opposite the carboxyl group by a member of the group consisting of radioiodinated histidyl, radioiodinated tyramyl, radioiodinated histamyl, and radioiodinated tyrosyl.

89. The method of claim 88 wherein the radioiodine is $^{125}I$.

90. The method of claim 88 wherein the fragment bound by said member is $hPTH^{65-84}$.

91. The method of claim 90 wherein the radioactively labeled fragment is $^{125}I\text{-}Tyr^{64}\text{-}hPTH^{65-84}$.

92. The method of claim 90 wherein the first antibody is chicken anti-$hPTH^{65-84}$ and the first buffering agent buffers the mixture to a pH in the range of about 7.5–8.6.

93. The method of claim 92 wherein the first buffering agent comprises a borate buffer with a pH of about 8.4.

94. The method of claim 92 wherein the first buffering agent comprises a BSA-borate buffer with a pH of about 8.4.

95. The method of claim 92 wherein the reaction of chicken anti-$hPTH^{65-84}$ with intact bovine PTH, C-terminal bovine PTH fragments, and said radioactively labeled fragment is allowed to proceed in the aforesaid manner by vortexing gently and incubating for 16 hours at 2°–8° C.

96. The method of claim 92 wherein the second antibody-precipitating complex is rabbit anti-chicken precipitating (RAC-PPT) complex and the second buffering agent buffers the mixture to a pH in the range of about 7.5–8.6.

97. The method in claim 96 wherein the second buffering agent comprises a borate buffer with a pH of about 8.4.

98. The method of claim 96 wherein the second buffering agent comprises a BSA-borate buffer with a pH of about 8.4.

99. The method of claim 96 wherein the reaction of RAC-PPT complex with the chicken anti-$hPTH^{65-84}$ bound radioactively labeled $hPTH^{65-84}$ is allowed to proceed in the aforesaid manner by vortexing and incubating for a minimum of 2 hours at room temperature or greater than than 16 hours at 2°–8° C.

100. The method of claim 81 wherein said double antibody radioimmunoassay comprises:
   A. Adding, to a measured quantity of the biological or other fluid to be assayed:
      1. a first antibody, which has a substantially high affinity for intact bovine PTH, C-terminal bovine PTH fragments, and later to be added radioactively labeled fragment, in a sufficient quantity to bind a significant quantity of the intact bovine PTH and C-terminal bovine PTH fragments in the biological or other fluid; and
      2. a first buffering agent to buffer the mixture to a pH suitable for reaction of the first antibody with intact bovine PTH, C-terminal bovine PTH fragments, and later to be added radioactively labeled fragment;
   B. Allowing reaction of the intact bovine PTH and C-terminal bovine PTH fragments with the first antibody to proceed substantially to equilibrium to thereby produce first antibody bound intact bovine PTH and first antibody bound C-terminal bovine PTH fragments;
   C. Adding a radioactively labeled fragment within the range of about 65–84 of bovine PTH or hPTH, in sufficient quantity to give a measurable counting rate of later formed precipitated second antibody bound first antibody bound radioactively labeled fragment;
   D. Allowing reaction of the radioactively labeled fragment with the first antibody bound intact bovine PTH and first antibody bound C-terminal bovine PTH fragments to proceed substantially to equilibrium to thereby bind a portion of the radioactively labeled fragment while freeing a portion of the bound intact bovine PTH and C-terminal bovine PTH fragments;
   E. Adding:
      1. a second antibody-precipitating complex, wherein the second antibody has a substantially high affinity for the first antibody, as bound to the radioactively labeled fragment, in a sufficient quantity to give a measurable counting rate of precipitated second antibody bound first antibody bound radioactively labeled fragment; and
      2. a second buffering agent to buffer the mixture to a pH suitable for reaction of the second antibody with first antibody bound radioactively labeled fragment;
   F. Allowing reaction of the second antibody-precipitating complex with the first antibody bound radioactively labeled fragment to proceed substantially to equilibrium to thereby produce precipitated second antibody bound first antibody bound radioactively labeled fragment;
   G. Separating the precipitated from non-precipitated radioactively labeled fragment;
   H. Measuring the radioactivity of the precipitated and/or non-precipitated radioactively labeled fragment;
   I. Correlating the respective measured radioactivity of the precipitated and/or non-precipitated radioactively labeled fragment for the biological or other fluid with that for known standards.

101. The method of claim 100 wherein the biological or other fluid is bovine serum or plasma.

102. The method of claim 100 wherein precipitated is separated from non-precipitated radioactively labeled fragment by centrifuging until the supernatant is substantially clear of the precipitate, and decanting the supernatant.

103. The method of claim 100 wherein the reaction of the first antibody with intact bovine PTH and C-terminal bovine PTH fragments is allowed to proceed in the aforesaid manner by vortexing gently and incubating the vortexed material until the reaction proceeds substantially to equilibrium.

104. The method of claim 100 wherein said reaction of the radioactively labeled fragment with the first antibody bound intact bovine PTH and first antibody bound C-terminal bovine PTH fragments is allowed to proceed in the aforesaid manner by vortexing gently and incubating the vortexed material until the reaction proceeds substantially to equilibrium.

105. The method of claim 100 wherein the reaction of the second antibody-precipitating complex with the first antibody bound radioactively labeled fragment is allowed to proceed in the aforesaid manner by vortexing gently and incubating the vortexed material until the reaction proceeds substantially to equilibrium.

106. The method of claim 100 wherein said correlation comprises:
A. Preparing a standard curve for which known standards are plotted respectively against the measured radioactivity of their precipitated and/or non-precipitated radioactively labeled fragment; and
B. Correlating via the standard curve the quantity of intact bovine PTH and C-terminal bovine PTH fragments in the biological or other fluid with the measured radioactivity of its precipitated and/or non-precipitated radioactively labeled fragment.

107. The method of claim 100 wherein the radioactively labeled fragment within the range of about 65–84 of bovine PTH or hPTH comprises the fragment bound at the end opposite the carboxyl group by a member of the group consisting of radioiodinated histidyl, radioiodinated tyramyl, radioiodinated histamyl, and radioiodinated tyrosyl.

108. The method of claim 107 wherein the radioiodine is $^{125}I$.

109. The method of claim 107 wherein the fragment bound by said member is $hPTH^{65-84}$.

110. The method of claim 109 wherein the radioactively labeled fragment is $^{125}I\text{-}Tyr^{64}\text{-}hPTH^{65-84}$.

111. The method of claim 109 wherein the first antibody is chicken anti-$hPTH^{65-84}$ and the first buffering agent buffers the mixture to a pH in the range of about 7.5–8.6.

112. The method of claim 111 wherein the first buffering agent comprises a borate buffer with a pH of about 8.4.

113. The method of claim 111 wherein the first buffering agent comprises a BSA-borate buffer with a pH of about 8.4.

114. The method of claim 111 wherein the reaction of chicken anti-$hPTH^{65-84}$ with intact bovine PTH and C-terminal bovine PTH fragments is allowed to proceed in the aforesaid manner by vortexing gently and incubating for a minimum of 4 hours at 2°–8° C.

115. The method of claim 111 wherein the reaction of the radioactively labeled fragment with the first antibody bound intact bovine PTH and first antibody bound C-terminal bovine PTH fragments is allowed to proceed in the aforesaid manner by vortexing gently and incubating for at least 20 hours at 2°–8° C.

116. The method of claim 111 wherein the second antibody-precipitating complex is rabbit anti-chicken precipitating (RAC-PPT) complex and the second buffering agent buffers the mixture to a pH in the range of about 7.5–8.6.

117. The method of claim 116 wherein the second buffering agent comprises a borate buffer with a pH of about 8.4.

118. The method of claim 116 wherein the second buffering agent comprises a BSA-borate buffer with a pH of about 8.4.

119. The method of claim 116 wherein the reaction of RAC-PPT complex with the chicken anti-$hPTH^{65-84}$ bound radioactively labeled fragment is allowed to proceed in the aforesaid manner by vortexing and incubating for a minimum of 2 hours at room temperature or greater than 16 hours at 2°–8° C.

* * * * *